(12) United States Patent
Anderson et al.

(10) Patent No.: US 8,642,631 B2
(45) Date of Patent: Feb. 4, 2014

(54) METHODS OF TREATING MAMMALS WITH EUSTACHIAN TUBE DYSFUNCTIONS

(75) Inventors: Colin Russell Anderson, Northcote (AU); Burkhard Franz, Melbourne (AU)

(73) Assignee: University of Melbourne, Victoria (AU)

( * ) Notice: Subject to any disclaimer, the term of this patent is extended or adjusted under 35 U.S.C. 154(b) by 175 days.

(21) Appl. No.: 12/994,709

(22) PCT Filed: May 27, 2009

(86) PCT No.: PCT/AU2009/000664
§ 371 (c)(1),
(2), (4) Date: Mar. 17, 2011

(87) PCT Pub. No.: WO2009/143572
PCT Pub. Date: Dec. 3, 2009

(65) Prior Publication Data
US 2011/0166190 A1 Jul. 7, 2011

(30) Foreign Application Priority Data
May 27, 2008 (AU) ................................ 2008902659

(51) Int. Cl.
*A61K 31/44* (2006.01)

(52) U.S. Cl.
USPC ...................................................... 514/357

(58) Field of Classification Search
USPC ........................................................ 514/357
See application file for complete search history.

(56) References Cited

U.S. PATENT DOCUMENTS

| | | | |
|---|---|---|---|
| 4,073,883 A | 2/1978 | Yasuda et al. | |
| 4,159,332 A | 6/1979 | Bollenbacher | |
| 4,229,428 A | 10/1980 | Cherqui et al. | |
| 5,132,115 A | 7/1992 | Wolter et al. | |
| 6,156,294 A * | 12/2000 | Mautone | 424/45 |
| 7,090,830 B2 | 8/2006 | Hale et al. | |
| 2002/0183297 A1 | 12/2002 | Niazi | |
| 2003/0015196 A1 | 1/2003 | Hodges et al. | |
| 2003/0017114 A1 | 1/2003 | Rabinowitz et al. | |
| 2004/0101560 A1 | 5/2004 | Sawchuk et al. | |
| 2004/0185001 A1 | 9/2004 | Rabinowitz et al. | |
| 2006/0073217 A1 | 4/2006 | Barak | |
| 2006/0240107 A1 | 10/2006 | Lenaerts et al. | |
| 2006/0246012 A1 | 11/2006 | Rabinowitz et al. | |
| 2007/0110805 A1 | 5/2007 | Levinson et al. | |
| 2007/0116729 A1 | 5/2007 | Palepu | |
| 2007/0165870 A1 | 7/2007 | Miller et al. | |
| 2007/0231390 A1 | 10/2007 | Dely et al. | |
| 2008/0004324 A1 | 1/2008 | Barak | |
| 2008/0066741 A1 | 3/2008 | LeMahieu et al. | |
| 2008/0261950 A1 | 10/2008 | Rupniak et al. | |
| 2010/0178331 A1 | 7/2010 | Nagata et al. | |

FOREIGN PATENT DOCUMENTS

| | | |
|---|---|---|
| CN | 1568986 A | 1/2005 |
| CN | 1732934 A | 2/2006 |
| EP | 0 502 642 A1 | 9/1992 |
| EP | 0 397 025 B1 | 1/1994 |
| FR | 2432313 | 2/1980 |
| GB | 0 945 095 | 12/1963 |
| GB | 1241906 A | 8/1971 |
| GB | 1 276 596 | 6/1972 |
| GB | 2 280 604 A | 2/1995 |
| JP | 06-219947 | 8/1994 |
| JP | 2001-064205 | 3/2001 |
| KR | 200855765 | 6/2008 |
| RU | 2308941 C1 | 10/2007 |
| WO | WO 00/53162 A1 | 9/2000 |
| WO | WO 02/43706 A2 | 6/2002 |
| WO | WO 02/064088 A2 | 8/2002 |
| WO | WO 02/094240 A1 | 11/2002 |
| WO | WO 03/026631 A1 | 4/2003 |
| WO | WO 03/077902 A1 | 9/2003 |
| WO | WO 03/101392 A2 | 12/2003 |
| WO | WO 03/105832 A1 | 12/2003 |
| WO | WO 2004/006903 A1 | 1/2004 |
| WO | WO 2004/037222 A2 | 5/2004 |
| WO | WO 2004/038428 A2 | 5/2004 |
| WO | WO 2004/089313 A2 | 10/2004 |
| WO | WO 2005/004850 A1 | 1/2005 |
| WO | WO 2005/011665 A1 | 2/2005 |
| WO | WO 2005/101979 A2 | 11/2005 |
| WO | WO 2006/106358 A2 | 10/2006 |
| WO | WO 2006/121979 A2 | 11/2006 |
| WO | WO 2007/002238 A2 | 1/2007 |
| WO | WO 2007/011707 A2 | 1/2007 |
| WO | WO 2007/076140 A2 | 7/2007 |

OTHER PUBLICATIONS

Laxdal et al., "Treatment of acute otitis media: a controlled study of 142 children", Canadian Medical Association Journal, vol. 102, No. 3, pp. 263-268.*
International Search Report and Written Opinion for International Patent Application No. PCT/AU2009/0006664, dated Jul. 31, 2009, 7 pages.
European search report for Application No. 09753336.8 dated May 25, 2011.

(Continued)

*Primary Examiner* — Kevin E Weddington

(57) ABSTRACT

The invention relates to methods of medically treating mammals with Eustachian tube dysfunctions, such as Ménière's disease, vertigo, Otitis Media (including Otitis Media with Effusion (OME), Acute Otitis Media (AOM) and Aerotitis Media (AM)) as well as other disorders which are characterized by ET dysfunction.

19 Claims, 8 Drawing Sheets

(56) References Cited

OTHER PUBLICATIONS

Cirek et al., (2005), "Efficacy and tolerability of a fixed combination of cinnarizine and dimenhydrinate versus betahistine in the treatment of otogenic vertigo: a double-blind, randomised clinical study," Clinical Drug Investigation 25(6):377-389.

Database WPI Week 199436, Thomson Scientific, London, GB; AN 1994-290844, XP002636973, & JP 6 219947 A (Kinki Daigaku GH) Aug. 9, 1994.

Strupp et al., (2008), "Long-term prophylactic treatment of attacks of vertigo in Menière's disease—comparison of a high with a low dosage of betahistine in an open trial," Acta Oto-Laryngologira 128:520-524.

Stupp et al., (1976), "Treatment of Menière's disease with betahistine," HNO 2(9):320-325.

Shelton et al., "Histamine Receptors in the Human Nose," Clin. Otolaryngol., 1994, 19, 45-49.

Регистр Лекарственных средств России:

Ежегодный сборник,, выпуск 106 2003 г., с. 140 (Register of Russian medicaments. Annual index. Issue 10, 2003, p. 140) (in Russian only).

\* cited by examiner

METHODS OF TREATING MAMMALS WITH EUSTACHIAN TUBE DYSFUNCTIONS

CROSS-REFERENCE TO RELATED APPLICATIONS

This application is a national stage application under 35 U.S.C. §371 of International Application No. PCT/AU2009/000664, filed May 27, 2009, which in turn claims priority to Australian Patent Application Serial No. 2008/902659, filed on May 27, 2008, the contents of each of which are incorporated herein by reference in their entirety.

FIELD OF INVENTION

The present invention relates generally to methods of medically treating mammals (including humans) and in particular methods of treating mammals with Eustachian tube dysfunctions. The invention also relates to the manufacture of medicaments for the treatment of Eustachian tube dysfunctions.

BACKGROUND OF INVENTION

The Eustachian tube ('ET'), also often referred to as the 'auditory tube' connects the middle ear cavity to the back of the nose/throat (nasopharynx). The ET is a tube a third of which is made of bone, the rest cartilage. In a human, the ET is normally closed with its wall collapsed, but it can open to let some air through in order to equalise the pressure between the middle ear and the outside environment. Opening in this way may be accomplished by swallowing, yawning, or chewing. The inability to voluntarily regulate or attain pressure equalisation (for instance, during aircraft flights, underwater diving, or due to certain disease states) creates a blockage which is often referred to as ET dysfunction.

The ET also serves to drain mucus or fluid from the middle ear. The ability of the ET to act as an efficient drain diminishes when blocked by pressure imbalances. Blockages of this nature may occur from upper airway infections or from allergic responses. The most common symptom of ET blockage is earache which is often more prevalent in children because the ET is shorter and more horizontal, the latter makes drainage of fluid harder. Also, depending on the severity of the blockage there may also be various levels of hearing impairment associated with ET blockage. There are also children born with an inherent weakness of Eustachian tube function. This may be a genetic phenomenon.

There are a number of diseases in which Eustachian tube dysfunction represents the primary underlying pathological mechanism and hence represent potential therapeutic indications. The most common group of therapeutic indications is Otitis Media (OM) otherwise known as inflammation of the middle ear.

OM has various attributes and while terminology and definitions are not universally agreed, it is possible to describe the following:

Acute Otitis Media (AOM) is characterised by rapid onset and short duration of signs and symptoms which may be local (such as otalgia) and/or systemic (fever and vomiting). During the early phases of infection, AOM may not be associated with effusion (fluid in the middle ear). However, effusion is a consequence of AOM. Relief of symptoms generally occurs before clearance of effusion.

Otitis Media with Effusion (OME) (also known as Serous Otititus Media, Secretory Otitus Media or by the lay term as "glue ear") occurs when a blockage in the eustachian tube leads to negative pressure in the middle ear and a transudate of fluid drawn from middle ear mucosa. The effusion may be serous, mucoid or purulent (or a combination of these). OME may follow AOM or occur without prior AOM. OME is often longer lasting (subacute or chronic) and often asymptomatic.

OME is usually treated by inserting small tubes (called ventilation tubes) into the tympanic membrane (or ear drum), which facilitates drainage of any accumulated fluid in the middle ear, and also continually equalizes the pressure in the middle ear. Unfortunately however, the insertion of ventilation tubes in this manner requires invasive surgical intervention. In addition, keeping the ET open with ventilation tubes also increases the risk of infection from the environment and via the ET, due to the loss of an air cushion.

Aerotitis Media (AM), (also known as barotrauma or "ear block") occurs following an increase in ambient air pressure such as when flying or during the use of a hypobaric chamber. The resulting pressure differential between the middle ear and atmosphere stretches the tympanic membrane producing discomfort or pain. Other symptoms may include slight hearing loss, sensation of fullness in ears and dizziness.

OM is a major world wide health problem. It is the most common illness for which children receive medical care in the United States and in most of the developed and developing countries in the world. Statistics indicate that 24.5 million physician's office visits were made for OM in the United States alone in 1990, representing a >200% increase over those reported in the 1980s. It is estimated that 83% of all children will experience at least one episode of acute OM (AOM) by 3 years of age and that more than 40% of children will experience three or more episodes of AOM by this age. Although only very rarely associated with mortality any longer, the morbidity associated with OM is significant. Otitis media with effusion (OME) is the commonest cause for acquired hearing loss in childhood with behavioural, educational, and language development delays being additional consequences of its early-onset.

Apart from the surgical solutions referred to above depending upon the cause and severity of the symptoms associated with ET dysfunction, physicians may prescribe decongestants, antihistamines or steroids. Decongestants and antihistamines are believed to reduce swelling of the mucosa, but there is no scientific proof that decongestants or antihistamines facilitate Eustachian tube function. Steroids have the disadvantage that they are potentially associated with severe side effects.

The present invention is directed to providing an effective treatment for ET dysfunctions which beneficially relieves some or all of the symptoms associated ET disorders or dysfunctions.

SUMMARY OF THE INVENTION

In one aspect the invention provides a method for treating Eustachian tube dysfunction (such as Otitis Media) including the step of topically applying to a patient an effective amount of betahistine.

In a further aspect the invention provides a topical composition comprising betahistine for the treatment of Eustachian tube dysfunction.

In a further aspect the invention provides the use of betahistine in the manufacture of a medicament for treating Eustachian tube dysfunctions wherein the medicament is to be topically applied to the Eustachian tube of a subject in need thereof.

In still a further aspect the invention provides the use of betahistine in the manufacture of a medicament in the form of a topical composition for the treatment of Eustachian tube dysfunctions.

In yet a further aspect the invention provides a topical composition comprising betahistine in the form of nose drops or a metered nasal spray for the treatment of Eustachian tube dysfunctions.

DETAILED DESCRIPTION OF INVENTION

Figure 1:
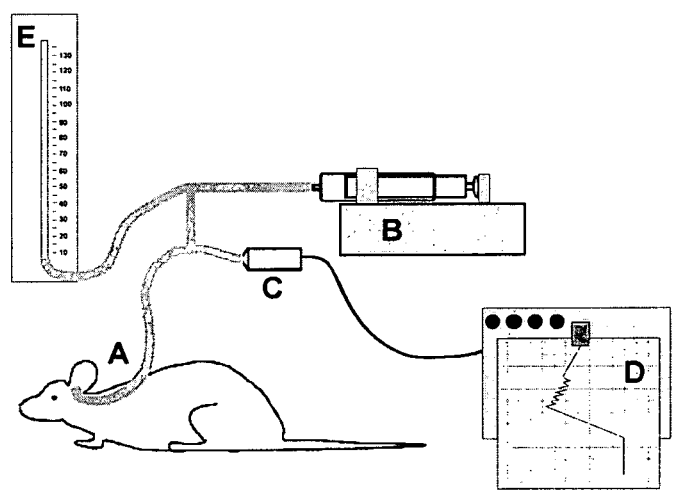
FIG. 1: An illustration of an experimental protocol which may be used to monitor the Eustachian tube function in a rat model.

Betahistine has been used systemically in the treatment of Ménière's disease. It is available under the brand name SERC® (Solvay Pharma Inc) as 8 mg, 16 mg and 24 mg tablets. Meniere's disease is a balance disorder which is characterised by symptoms such as episodic vertigo, ringing in the ear (tinnitus), a feeling of fullness or pressure in the ear, hearing loss, nausea and vomiting, The exact mechanism of action of betahistine (or main location of action) in the treatment of Ménière's disease is unclear. Being reported as a histamine like drug, multiple effects have been postulated. It is generally accepted, however, that its action on the vascular system will bring about beneficial oxygenation to the inner ear. Suppression of an overexcited vestibular system in the peripheral organ and dampening central neural mechanisms are also postulated as possible therapeutic effects.

Although betahistine is believed to have similar action to histamine, experiments conducted by the present inventors suggest that its action on ET is different to histamine. This is contrary to reports that observe aggravated ET function in humans administered with histamine (see Walker S B, Shapiro G G, Bierman C W, Morgan M S, Marshall S G, Furukawa C T, Pierson W E. Induction of Eustachian tube dysfunction with histamine nasal provocation. J Allergy Clin Immunol 76: 158-162, 1985; Skoner D P, Doyle W J, Fireman P. Eustachian tube obstruction (ETO) after histamine nasal provocation—a double-blind dose-response study. J Allergy Clin Immunol 79: 27-31, 1987; Downs B W, Butehorn H F 3rd, Prazma J, Rose A S, Stamat J C, Pillsbury H C 3rd. Otolaryngol Head Neck Surg 124: 414-420, 2001). The present invention is predicated (in part) on the discovery that, contrary to the teaching of the prior art, betahistine may exert at least some of its beneficial effects in Ménière's disease and other imbalance disorders by targeting the functioning of the ET. More specifically, the invention is based on the discovery that betahistine when administered topically to the ET, effectively improves ET functions in mammals.

As used herein the term "Eustachian tube dysfunction" or "Eustachian tube disorder" refers to the hypofunction of the Eustachian tube. The hypofunction is directly related to the inability of a subject to equalise pressure between the middle ear and the external environment. Long-term hypofunction of the ET can lead to the accumulation of mucus or fluid in the middle ear space. The continued absorption of oxygen further increases the pressure in the middle ear. ET dysfunction may occur as a result of illness such as a bacterial infection (such as a common cold) or viral infection (such as influenza). Pollutions and other allergens may also be responsible for ET dysfunction. Obesity can also predispose a person to ET dysfunction because excess fatty deposits around the passageway of the ET may serve to narrow the ET making obese persons more susceptible to ET blockage. ET dysfunction may also occur where there is a sudden or prolonged change is pressure, such as during airplane travel or underwater diving. Other conditions, such as nasal polyps, a cleft palate, or a skull based tumor are also often characterised with ET dysfunction. The present invention also contemplates the use of the present invention in the treatment of Ménière's disease, vertigo, Otitis Media (including AOM, OME and AM) or other disorders which are characterised with ET dysfunction.

In an embodiment the invention specifically contemplates the use of betahistine applied topically in the treatment of OM and more particularly Otitis Media with Effusion (OME).

Whilst OME may occur in both adults and children, it is of particular concern in children as it can result in hearing impairment and lead to learning difficulties and language development problems. As such in an embodiment, the invention is directed to the treatment of OME in a human child.

Also, as used herein the terms "topical", "topically applying", and the like relates to the act of applying a medicament or composition to a body surface. In relation to the present invention, the body surface is the nasal mucosa nasopharynx and the openings of the Eustachian tubes. Topical medicaments or compositions for use in the present invention are presented in the form of ointments, creams, gels, drops, pastes, powders and spray dose forms. In relation to the present invention the site of administration of the topical compositions or medicaments is preferably via the nose.

Without wanting to be bound by theory the effect exhibited by betahistine on the ET suggests that betahistine acts on a different range of receptors in the ET compared to histamine. Betahistine is a strong H3 receptor antagonist and a relatively weak (much weaker than histamine) H1 agonist. H3 receptors are exclusively associated with nervous tissue, particularly nerve terminals, where their activation inhibits neurotransmitter release. This applies to parasympathetic, sympathetic and nociceptive terminals, which are all present in the walls of the ET and are potentially capable of influencing ET function via a change in glandular secretion that facilitates ET opening.

One benefit of topically applying betahistine is that it is administered to the site where action is sought. In this regard, and again without wanting to be bound by theory, the topical application of betahistine coming into contact with the ET is thought to lead to the modification of surface tension and enhances ET opening function.

As another advantage, topical application will also need far lower doses than systemic application, therefore side effects are less likely to occur.

From studies conducted with Ménière's patients, it is known that the oral administration of betahistine can cause unpleasant side effects such as gastric upset, nausea, headache, skin rashes of various types, urticaria, and itching. It is proposed that through topically administering betahistine according to the present invention at least some, if not all, of these side effects may be avoided or at the very least minimised.

Reference herein to "treating" or "treatment" are to be understood to include prophylactic or preventative treatment, as well as therapeutic treatment.

The invention is directed to topical applications of betahistine for the treatment of ET dysfunctions. As used herein reference to "betahistine" includes the compound N-methyl-2-pyridineethanaamine (synonyms include: 2-[2-(methylamino)ethyl]pyridine and [2-(2-pyridyl)ethyl]methylamine) in free base form, salt form (formed by the reaction of the free-base with a pharmaceutically acceptable inorganic or organic acid) or in pro-drug form. Salt forms include the hydrochloride (including dihydrochloride), hydrobromide, methanesulfonate, toluenesulphonate, fumarate, maleate, acetate, lactate, malonate, citrate, ascorbate, tartrate, and propionate salts.

The administered betahistine or the betahistine used to prepare the topical compositions of the present invention may be in liquid form, amorphous form, crystalline form and/or in the form of solvates (e.g. hydrates) and it is intended that all forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The betahistine may also be administered in a derivatised "pro-drug" form. The term "pro-drug" is used in its broadest sense and encompasses those derivatives that are converted in vivo to betahistine. Such derivatives would readily occur to those skilled in the art, and include, for example, where the ring nitrogen atom is converted to an N-oxide or where the free amino group is converted to an amide. Any betahistine derivative that is a prodrug of betahistine as referred to above is within the scope and spirit of the invention.

Thus the invention also includes, when possible, the free-base form, salt form, or a pharmaceutically acceptable derivative of betahistine such as a solvate and/or prodrugs thereof.

Betahistine is to be administered to the subject in a treatment effective amount. As used herein, a treatment effective amount is intended to include at least partially attaining the desired effect, or delaying the onset of, or inhibiting the progression of, or halting or reversing altogether the onset or progression of one or more symptoms associated with ET dysfunction including fullness or pressure in the ear (which may be caused by fluid build up), vertigo, imbalance, hearing loss, nausea, and vomiting.

As used herein, the term "effective amount" relates to an amount of betahistine which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another preferred embodiment, the dosage may be in the range of 1 mg to 100 mg per kg of body weight per dosage, such as up to 50 mg per body weight per dosage.

In one embodiment an effective concentration of betahistine may be between 0.1 mg/mL to 100 mg/mL betahistine (calculated from free-base)/carrier applied within the nasopharynx.

In another embodiment an effective concentration of betahistine (calculated from free-base)/carrier may be between 0.1 to 50 mg/mL, for instance, 0.5 to 10 mg/mL, 0.5 to 30 mg/mL, 0.5 to 20 mg/mL, 0.5 to 15 mg/mL or 0.5 to 10 mg/mL.

In another embodiment an effective concentration of betahistine may be up to 10 mg/mL betahistine (calculated from free-base)/carrier applied within the nasopharynx, for instance 2, 3, 4, 5, 6, 7, 8 or 9 mg/mL.

Suitable dosage amounts and dosing regimens can be determined by the attending physician and may depend on the particular condition being treated, the severity of the condition as well as the general age, health and weight of the subject. Preferred unit dosage compositions are those containing a daily dose or unit, daily sub-dose, as herein above described, or an appropriate fraction thereof, of the active ingredient.

The betahistine according to the present invention may be administered in a single dose or a series of doses. While it is possible for the active ingredient to be administered alone, it is preferable to present it as a composition, specifically as a topical composition. The formulation of such topical compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like.

It will be understood that the topical compositions of the invention may also include other supplementary physiologically active agents. These may include mucolytic or decongestant agents, for example, Acetylcysteine, Bromhexine, Carbocisteine, Eprazinone, Mesna, Amroxol, Sobrerol, Domiodol, Letosteine, Stepronin, Tiopronin, Dornase alfa, Neltenexine, Erdosteine, pseudoephedrine, phenylephrine, phenylpropanolamine and oxymetazoline.

Compositions suitable for topical administration to the ET may comprise betahistine with or without other active agents dissolved or suspended in any suitable carrier or base and may be in the form of lotions, drops, gel, creams, pastes, ointments and the like. Suitable carriers include ethanol, mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water.

Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Solutions or suspensions may be applied directly to the nasal cavity by conventional means, for example with a dropper, pipette or spray. The formulations may be provided in single or multidose form. In the case of a dropper or pipette, this may be achieved by the patient administering an appropriate, predetermined volume of the solution or suspension.

In the case of a spray, this may be achieved, for example, by means of a metering atomising spray pump. To improve nasal delivery and retention the betahistine may be encapsulated with cyclodextrins, or formulated with other agents expected to enhance delivery and retention in the nasal mucosa.

Nasal administration may also be achieved by means of an aerosol formulation in which the betahistine is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of betahistine may be controlled by provision of a metered valve.

Alternatively the topical compositions comprising betahistine may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, for example, gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example, by micronisation.

When desired, formulations adapted to give sustained release of the active ingredient may be employed.

It should be understood that in addition to the active ingredients particularly mentioned above, the topical compositions of this invention may include other agents conventional in the art having regard to the type of composition in question, for example, those suitable for oral administration may include such further agents as binders, sweeteners, thickeners, flavouring agents, buffering agents, disintegrating agents, coating agents, preservatives, lubricants and/or time delay agents. Suitable sweeteners include sucrose, lactose, glucose, aspartame or saccharine. Buffer systems are routinely used to provide pH values of a desired range and include carboxylic acid buffers for example acetate, citrate, lactate and succinate. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, BHT, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Certain embodiments of the invention will now be described with reference to the following examples which are intended for the purpose of illustration only and are not intended to limit the scope of the generality hereinbefore described.

EXAMPLES

Method

Figure 2:
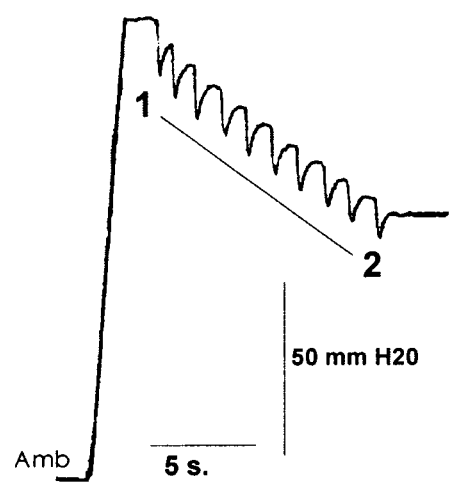
FIG. 2: A depiction of a pressure recording of Eustachian tube function in an anaesthetised rat.

Animal experiments were conducted on female and male adult Sprague Dawley rats weighing 250-450 g. Up to five animals were used in each section of the experiment. The experimental set up is shown in FIG. 1. In this figure, a small tube is glued into the tympanic bulla of an anaesthetised rat (A). The tube is connected to a syringe pump (B), a pressure transducer (C) and data recorder (D) and to a manometer (E). The syringe pump is used to increase pressure within the middle ear. The Eustachian tube is momentarily opened by electrically stimulating the superior laryngeal nerve and forcing reflex swallowing. An example of a pressure recording of Eustachian tube function in an anaesthetised rat is shown in FIG. 2. From this it can be seen that intra-bulla pressure was increased from ambient (Amb) to around 130 mm of water. From point 1 to point 2, the superior laryngeal nerve was stimulated, leading to ten reflex swallows, each one of which momentarily opened the Eustachian tube, leading to partial equalization of the pressure in the middle ear. The overall pressure drop is a measure of the efficiency of pressure equalisation via the Eustachian tube.

Each experiment consisted of a series of active Eustachian tube function tests preceded by a passive run. In the passive run pressure was increased in the bulla by a continuous air flow (30 ml/min) until the Eustachian tube opened spontaneously. While the air continued to flow, the pressure in the middle ear decreased until the Eustachian tube closed. Now the pressure in the middle ear, due to continued air flow, could build up again until the Eustachian tube opened a second time. This enabled the measurement of the passive opening and closing pressures of the Eustachian tube. The active runs consisted of three preceding control runs (C1-C3) followed by three runs assessing the effect of intervention S1-S6. At the start of each active run the pressure in the bulla was raised to 75% of the passive opening pressure of the Eustachian tube. At this point the air flow into the bulla was stopped. For active control of middle ear pressure, the superior laryngeal nerve was exposed and electrically stimulated with a bipolar hook electrode (1-3V, 10 Hz, 500 msec). This caused reflex swallowing, which was accompanied by a momentary opening of the Eustachian tube, and reduced middle ear pressure step by step. In each active run 10 consecutive swallows were recorded.

Prior to each active run 5 µl of betahistine dihydrochloride of an 8 mg/mL ethanol solution (from Solvay Pharma S.A.; Vasomotal) applied in a single bolus (total of 40 µg) were injected into the bulla and then flushed through the Eustachian tube (5 animals, FIG. 4), applied to the nasopharynx (5 animals FIG. 3) or 10 µl were injected peritoneally (5 animals FIG. 5). Five animals were treated with 5 µl normal saline applied to the nasopharynx and in five animals 5 µl normal saline was injected into the bulla. These latter served as a control. For each group of five animals, the raw data were first normalized with respect to the last control run prior to experimental manipulations and subjected to an arcsine transformation. The control and experimental results for each of the measurements were compared using unpaired t-tests, with $\alpha=0.05$.

Results

Figure 3:
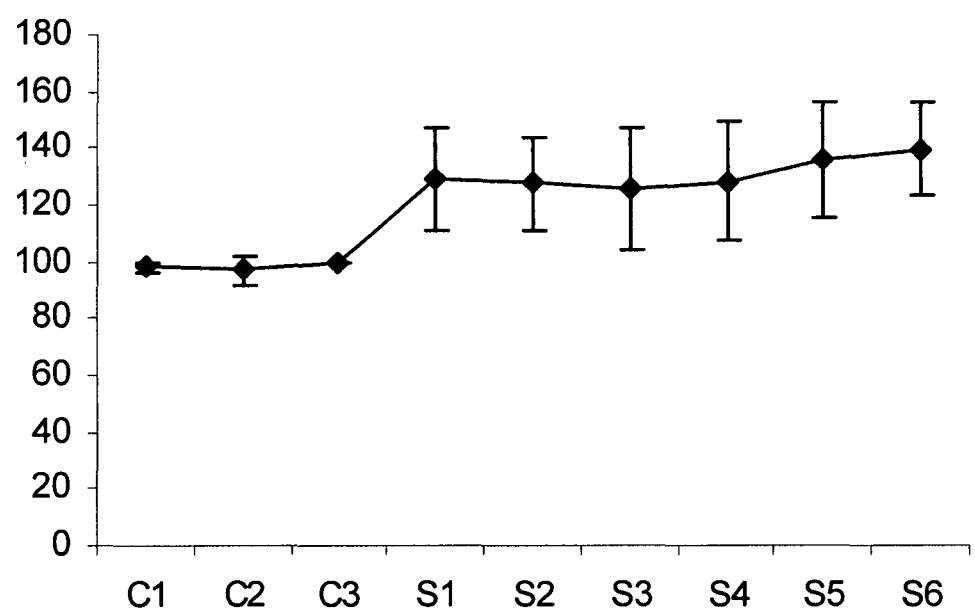
FIG. 3: A graph depicting the mean effect of betahistine diHCl (5 µl; Vasomotal) applied within the Eustachian tube on middle ear pressure equalisation (n=5, right ear; % proportional pressure change on swallowing versus trial number (C1-S6)).

FIG. 3 shows the effect of betahistine (applied within the nasopharynx) on efficiency of pressure equalisation through the Eustachain tube. For each trial (C1-S6, at 4 minute intervals), middle ear pressure was increased in healthy anaesthetised rats, then the drop in pressure monitored while they swallowed. After three control measurements (C1-3), betahistine diHCl was applied to the nasopharynx. The presence of betahistine in the nasopharynx increased the efficiency of pressure equalisation by an average 31%. All values are normalized to control measurement C3. Error bars=standard deviation.

Figure 4:
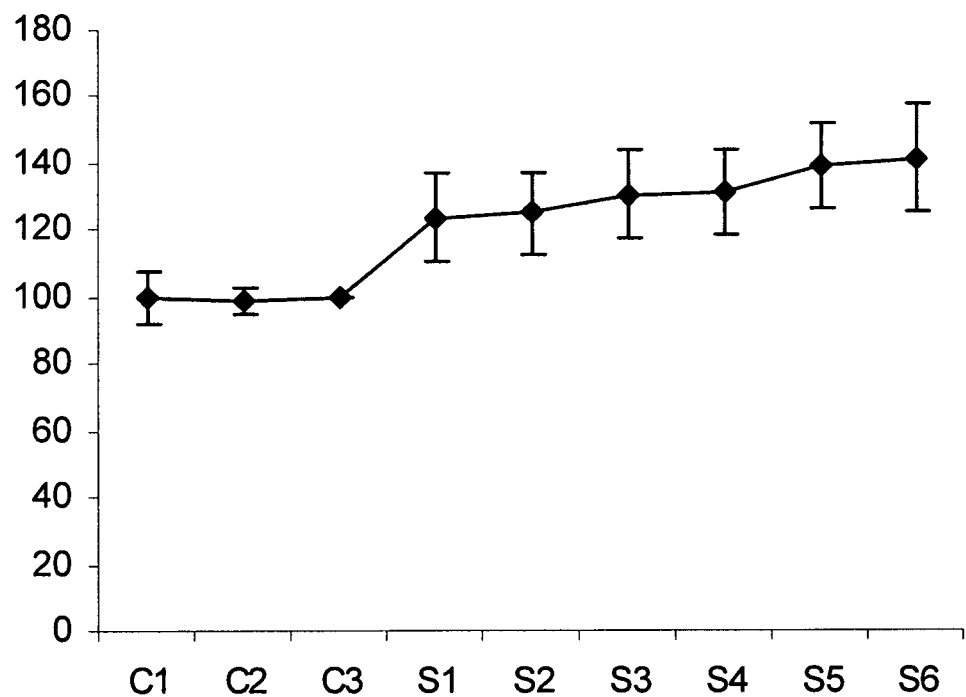
FIG. 4: A graph depicting the mean effect of betahistine diHCl (5 µl; Vasomotal) applied within the nasopharynx on middle ear pressure equalisation (n=4, right ear; % proportional pressure change on swallowing versus trial number (C1-S6)).

FIG. 4 demonstrates the same procedure as for FIG. 3, but betahistine is applied within the tympanic bulla and flushed through the Eustachian tube. Again, the presence of betahistine increased the efficiency of Eustachian tube pressure equalisation by around 30%.

Figure 5:
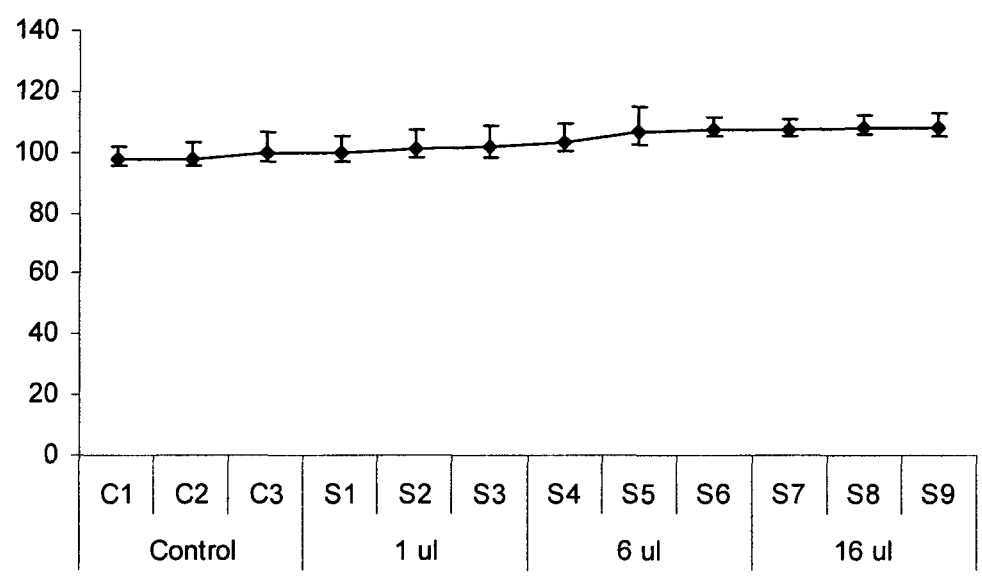
FIG. 5: A graph depicting the mean effect of betahistine diHCl applied systemically on middle ear pressure equalisation (n=5, right ear; % proportional pressure change on swallowing versus trial number (C1-S9))

FIG. 5 demonstrates an experiment where betahistine diHCl (Vasomotal) is injected systemically (intraperitoneal injection) in 5 animals. The doses were given cumulatively (1, 5 and 10 µl) for a total dose of 16 µl. The graph indicates no significant effect on ET function (note: each data point is 4 minutes apart).

Figure 6:
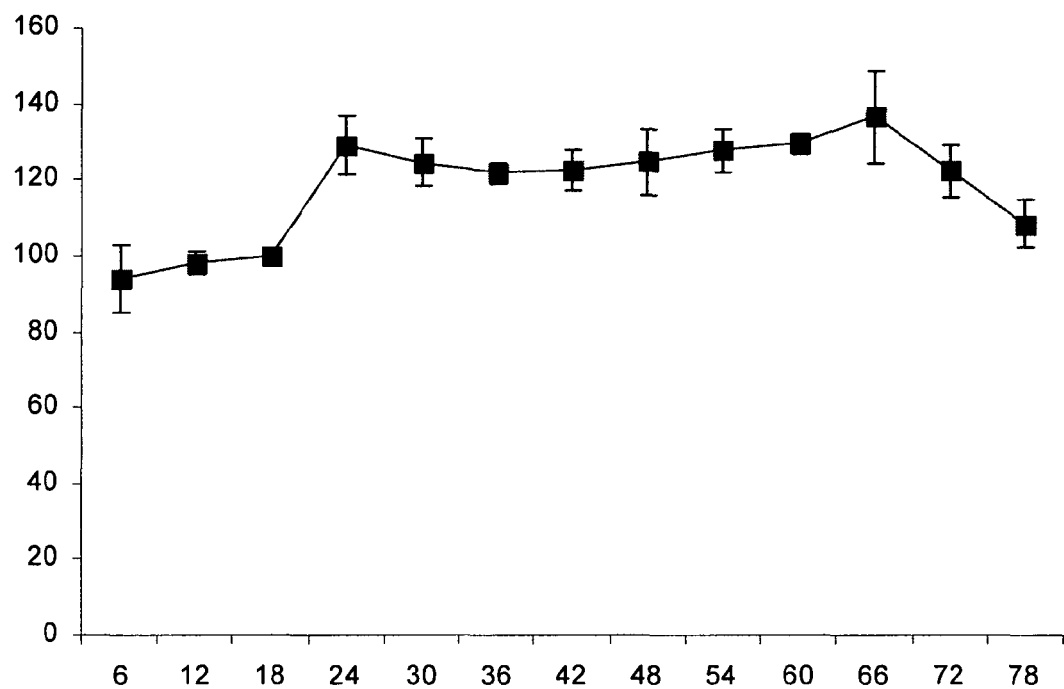
FIG. 6: A graph depicting the mean effect of 10 µl 4 mg/ml betahistine diHCl applied within the nasopharynx on middle ear pressure equalisation (n=4, right ear; response normalised to control versus time (min.)).

FIG. 6 is a graph depicting the mean results of a response/time study of 3 animals to 10 µl of 2 mg/mL betahistine diHCl. The first three readings are controls, betahistine was first added into the nasopharynx between 18 and 24 minutes.

Figure 7:
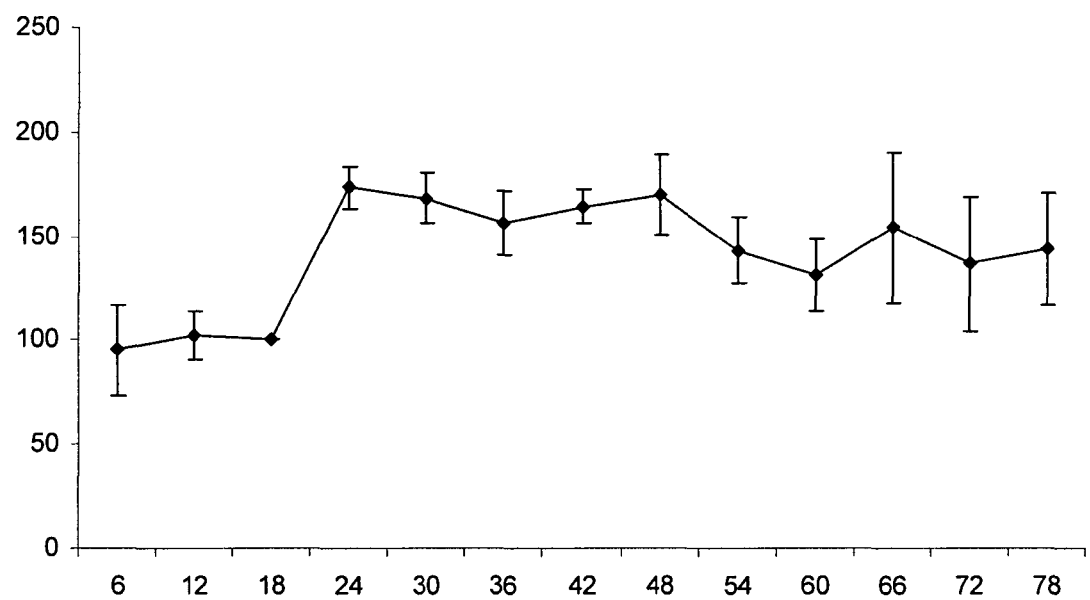
FIG. 7: A graph depicting the mean effect of 10 µl 2 mg/ml betahistine diHCl (n=3, +/−SEM; response normalised to control versus time (min.)).

FIG. 7 is a graph depicting the mean results of a response/time study of 3 animals to 10 µl of 4 mg/mL betahistine diHCl. The first three readings are controls, betahistine was first added into the nasopharynx between 18 and 24 minutes.

Figure 8:
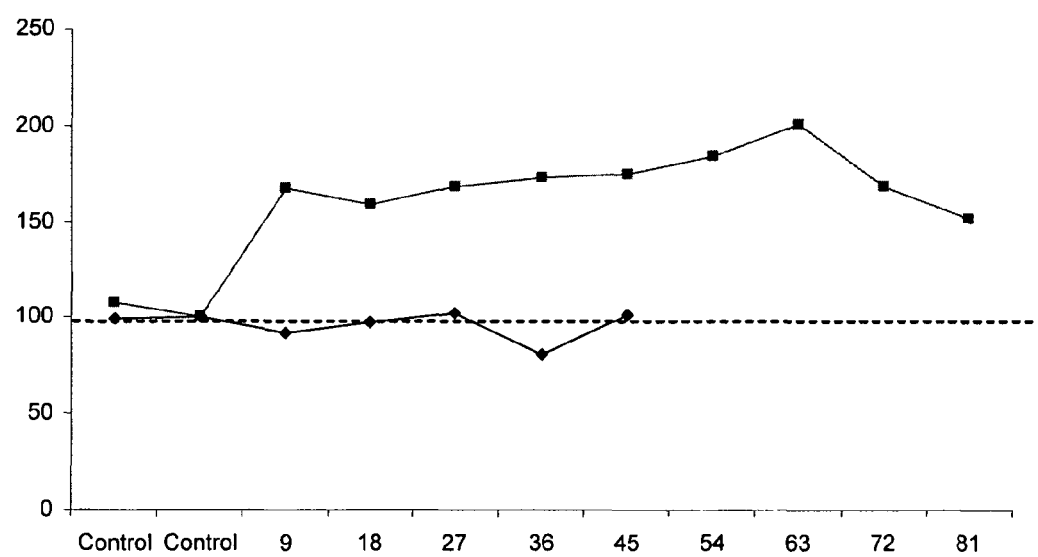
FIG. 8: A graph depicting the mean effect of 10 µl 8 mg/ml betahistine diHCl in a single animal (———■———) versus a single animal with saline (———◆———) applied within the nasopharynx (% of control versus time (mins) after betahistine/saline administration).

FIG. 8 is a graph depicting the results of a response/time study of 1 animal given 10 µl of 8 mg/mL into the nasopharynx versus 1 animal given only an equivalent volume of saline. In each case, the first three readings are controls, betahistine/saline was first added into the nasopharynx between 18 and 24 minutes.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. A method for treating Eustachian tube dysfunction comprising topically applying to a Eustachian tube of a patient in need thereof an effective amount of betahistine or a salt thereof, wherein the betahistine is formulated for use as nose drops, eye drops, or a metered nasal spray.

2. A method according to claim 1 wherein the betahistine or a salt thereof is administered to a nasal mucosa nasopharynx or an opening of the Eustachian tubes.

3. A method according to claim 1 wherein the betahistine or a salt thereof is administered at a concentration of betahistine (calculated from free-base) between 0.1 mg/mL to 50 mg/mL.

4. A method according to claim 1 wherein the Eustachian tube dysfunction is Otitis Media (OM).

5. A method according to claim 1 wherein the Eustachian tube dysfunction is Otitis Media with Effusion (OME).

6. A method according to claim 1 wherein the patient is a human child.

7. A method according to claim 1 wherein the Eustachian tube dysfunction is Acute Otitis Media (AOM) or Aerotitis Media (AM).

8. A method according to claim 1 wherein the betahistine is in a salt form.

9. A method according to claim 8 wherein the betahistine is in the dihydrochloric acid salt form.

10. A method according to claim 1 wherein the betahistine or a salt thereof is administered at a concentration of betahistine (calculated from free-base) of up to 10 mg/mL.

11. A method according to claim 1 further comprising administering a further pharmaceutically active agent.

12. A method of claim 11 wherein the further pharmaceutically active agent is a mucolytic or decongestant.

13. A method comprising topically administering to a patient in need thereof an effective amount of betahistine or a salt thereof, wherein the betahistine is formulated for use as nose drops, eye drops, or a metered nasal spray.

14. A method according to claim 13 wherein the betahistine or a salt thereof is administered at a concentration of betahistine (calculated from free-base) between 0.1 mg/mL to 50 mg/mL.

15. A method according to claim 14 wherein the betahistine or a salt thereof is administered at a concentration of betahistine (calculated from free-base) of up to 10 mg/mL.

16. A method according to claim 13 wherein the betahistine is in a salt form.

17. A method according to claim 16 wherein the betahistine is in the dihydrochloric acid salt form.

18. A method according to claim 13 further comprising administering a further pharmaceutically active agent.

19. A method of claim 18 wherein the further pharmaceutically active agent is a mucolytic or decongestant.

* * * * *